US00PP11028P

United States Patent [19]

Fazari

[11] Patent Number: Plant 11,028

[45] Date of Patent: Aug. 10, 1999

[54] HYBRID TEA ROSE PLANT NAMED 'FAZA 245'

[75] Inventor: Evelyne Fazari, Antibes, France

[73] Assignee: Bear Creek Gardens, Inc., Medford, Oreg.

[21] Appl. No.: 09/025,584

[22] Filed: Feb. 18, 1998

[51] Int. Cl.[6] ..... A01H 5/00

[52] U.S. Cl. ..... Plt./137

[58] Field of Search ..... Plt./137, 135, 130

*Primary Examiner*—Howard J. Locker

*Attorney, Agent, or Firm*—Klarquist Sparkman Campbell Leigh & Whinston, LLP

[57] ABSTRACT

Hybrid tea rose plant having good production of large, many petaled pink flowers on long stems, having good vase life.

1 Drawing Sheet

1

The present invention relates to a new and distinct variety of rose plant of the hybrid tea class which was originated by me by crossing an unnamed pink hybrid tea seedling (not patented), with an unnamed pink hybrid tea seedling (not patented).

The primary objective of this breeding was to produce a new rose variety having the long stems, good cut flower production, and pink flower color of the female unnamed seedling parent combined with the strong, straight stems and good cut flower production of the pink flowered, unnamed seedling male parent. The objective was substantially achieved, along with other desirable improvements, as evidenced by the following unique combination of characteristics that are outstanding in the new variety and that distinguish it from its parents, as well as from all other varieties of which I am aware:

1. Long, straight stems;
2. Good cut flow production;
3. Long vase life;
4. Attractive, pink flowers with many petals.

FAZA 245 was bred, selected, and tested as a greenhouse cut rose hybrid tea variety. Production of long, strong stems with large pink flowers are primary attributes. Stems with average 22–26 inches long and production in a greenhouse in Somis, Calif. will average 170 stems per square meter of greenhouse. This will equal 24–25 stems per plant per year.

Asexual reproduction of this new variety by budding, as performed at Somis and Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed pink hybrid tea seedling (unpatented).

*Pollen parent.*—Unnamed pink hybrid tea seedling (unpatented).

Classification:

*Botanical.*—Rosa hybrida.

*Commercial.*—Hybrid Tea.

2

FLOWER

Observations made from specimens grown in a greenhouse environment at Somis, Calif. from January, 1996–September 1997.

Blooming habit: Continuous.

Bud:

*Size.*—Two inches long when the petals start to unfurl.

*Form.*—The bud form is long, pointed ovoid.

*Color.*—When sepals first divide, bud color is Orange Group 29D. When half blown, the upper sides of the petals are Red Group 39C on the outer two-thirds of the petal changing to Orange Group 29C then to Yellow-Orange Group 14C toward the petal base; and the lower sides of the petals are Red Group 39D on the outer three-quarters of the petal changing to Yellow-Orange Group 14D on the inner one-quarter of the petal.

*Sepals.*—Color: Green Group 138B. Surface texture: Covered in fine hairs. There are three lightly to normally appendaged sepals. There are two unappendaged sepals with hairy edges.

*Receptacle.*—Color: Green Group 137D. Shape: Funnel. Size: Medium (⅜" long×¼" wide). Surface: Smooth.

*Peduncle.*—Length: Medium (3 to 3¼"). Surface: Smooth, with a few glands. Color: Medium green. Strength: Stiff, erect, and heavy.

Bloom:

*Size.*—Large. Average open size is four to four and one-half inches.

*Borne.*—Singly.

*Stems.*—Long (22–26").

*Form.*—When first open: High centered. Permanence: Retains its form to the end; outer petals curl slightly with some quilling.

*Petalage.*—Number of petals under normal conditions: 35–40.

*Color.*—The upper sides of the petals are Red Group 39C on the outer two-thirds of the petal changing to Orange Group 29C then to Yellow Group 14C toward the petal base. The reverse sides of the petals are Red Group 39D on the outer three-quarters of the petal changing to Yellow-Orange Group 14D on the inner one-quarter. The base of each petal has a small (⅛"×⅛"), yellow, Yellow Group 7C, half moon at the point of attachment. The major color on the upper side is Red Group 39C.

*Variegations.*—Occasional greenish-white streak on the guard petals.

*Discoloration.*—At the end of the first day: No change. At the end of the third day: No change. Remains constant in the vase through day twelve.

*Fragrance.*—Slight.

Petals:

*Texture.*—Thick.

*Shape.*—Round.

*Form.*—Tips slightly recurved, edges slightly quilled.

*Arrangement.*—Imbricated. Petaloids in the center are few.

*Persistence.*—Drop off cleanly before drying.

*Lastingness.*—On the plant: Long (eight days). As a cut flower: Long (twelve days).

Reproductive parts:

*Anthers.*—Size: Medium. Quantity: Many. Color: Yellow. Arrangement: Regular around styles.

*Filaments.*—Color: Yellow.

*Pollen.*—Color: Gold-yellow.

*Styles.*—Color: Greenish-white.

*Stigmas.*—Color: Greenish-white.

Plant:

*Form.*—Bush.

*Growth.*—Very vigorous; upright; branching; Height after one growing season in Somis, Calif. is six feet with the width three and one-half feet.

Foliage: Number of leaflets on normal mid-stem leaves: Five or seven.

*Size.*—Large. (6½"–7" long; 4½"–5" wide).

*Quantity.*—Abundant.

*Color.*—New foliage: Upper surface: Greyed-Purple Group 183A. Lower surface: Greyed-Purple Group 183C. Old foliage: Upper surface: Green Group 137A. Lower surface: Green Group 139C. The lower surface often will keep a purplish cast close to Greyed-Purple Group 185C.

*Shape.*—Broadly oval.

*Texture.*—Upper side: Smooth.

*Edge.*—Serrated.

*Serration.*—Single, small.

*Petiole rachis.*—Color: Green.

*Petiole underside.*—Smooth.

*Stipules.*—Medium (⅝"); serrated, bearded.

*Disease resistance.*—Susceptible to mildew under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary (¼" long). On laterals from main canes: Ordinary.

*Form.*—Medium; hooked downward.

*Color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by its good production of large, many petaled, pink flowers on long, strong stems having long vase life.

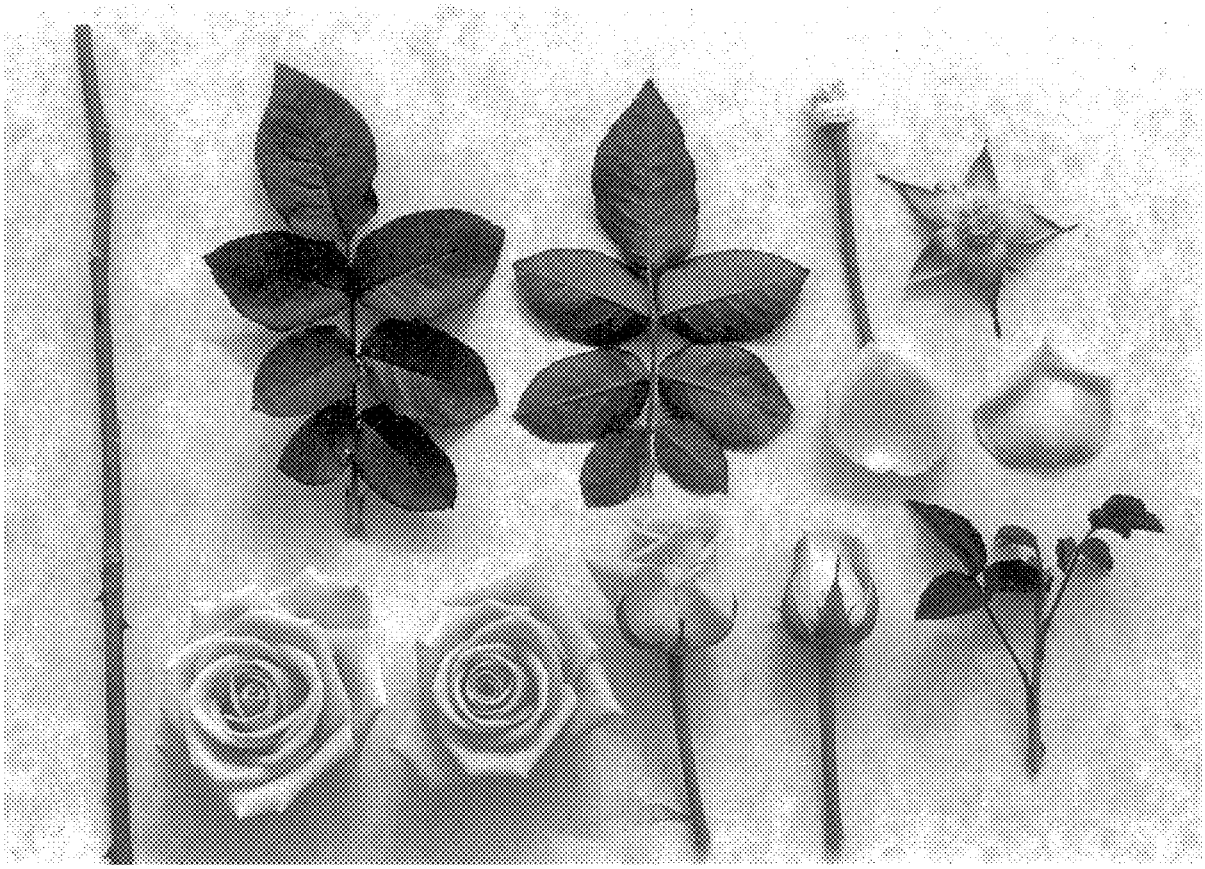

* * * * *